(12) United States Patent
Goble et al.

(10) Patent No.: US 7,052,494 B2
(45) Date of Patent: May 30, 2006

(54) SURGICAL SYSTEM AND METHOD

(75) Inventors: Colin C O Goble, Egham (GB); Mark G Marshall, Winnersh (GB)

(73) Assignee: Gyrus Medical Limited, Cardiff (GB)

( * ) Notice: Subject to any disclaimer, the term of this patent is extended or adjusted under 35 U.S.C. 154(b) by 166 days.

(21) Appl. No.: 10/245,378

(22) Filed: Sep. 18, 2002

(65) Prior Publication Data

US 2003/0060862 A1     Mar. 27, 2003

(30) Foreign Application Priority Data

Sep. 21, 2001   (GB) ............................... 0122833.7

(51) Int. Cl.
*A61B 18/18*   (2006.01)
(52) U.S. Cl. ........................... 606/45; 606/48; 606/49; 606/50
(58) Field of Classification Search .................. 606/41, 606/42, 45–50; 604/22, 35; 600/105, 135; 128/898
See application file for complete search history.

(56) References Cited

U.S. PATENT DOCUMENTS

| 3,945,375 | A |   | 3/1976 | Banko |   |
|---|---|---|---|---|---|
| 5,176,677 | A |   | 1/1993 | Wuchinich |   |
| 5,190,541 | A | * | 3/1993 | Abele et al. | 606/46 |
| 5,277,696 | A |   | 1/1994 | Hagen |   |
| 5,312,399 | A | * | 5/1994 | Hakky et al. | 606/15 |
| 5,527,331 | A |   | 6/1996 | Kresch et al. |   |
| 5,885,243 | A |   | 3/1999 | Capetan et al. |   |
| 5,904,681 | A |   | 5/1999 | West, Jr. |   |
| 6,032,673 | A | * | 3/2000 | Savage et al. | 128/898 |
| 6,159,209 | A |   | 12/2000 | Hakky |   |
| 6,193,715 | B1 |   | 2/2001 | Wrublewski et al. |   |
| 6,214,001 | B1 |   | 4/2001 | Casscells et al. |   |
| 6,270,497 | B1 |   | 8/2001 | Sekino et al. |   |
| 6,702,810 | B1 | * | 3/2004 | McClurken et al. | 606/34 |
| 2002/0107516 | A1 | * | 8/2002 | Sharkey et al. | 606/49 |

FOREIGN PATENT DOCUMENTS

| DE | 299 14 180 | 5/2000 |
|---|---|---|
| EP | 0 282 684 A1 | 9/1988 |
| WO | WO 97/33523 | 9/1997 |

* cited by examiner

*Primary Examiner*—Rosiland Rollns
(74) *Attorney, Agent, or Firm*—Oliff & Berridge, PLC

(57) ABSTRACT

A surgical instrument comprises at least two elongate hollow tubes (14, 15), each having an aperture (18) at the distal end portion. The inner tube (14) is disposed within the other tube (15), and is mounted for rotation about its longitudinal axis. A cutting tool (4) is located at the distal end of the tube (14), and is positioned adjacent to the apertures (18). A motor (5) is provided for rotating the inner tube (14), and the inner tube (14) has a central lumen (21) through which tissue cut by the cutting tool (4) is removed under the action of a source of suction (12). Heat is supplied to the tissue, prior to, or simultaneously with, the cutting thereof, such that the tissue being cut by the cutting tool (4) is coagulated tissue. In one embodiment, there is a third tube (16), and saline is fed to the apertures (18) via a channel (19) between the tubes (15) and (16). The outer tube (16) constitutes an active electrode, and the inner tube (14) constitutes the return electrode of an electrosurgical device. A radio frequency signal, supplied to the electrosurgical device, causes tissue to be coagulated prior to being cut by the cutting tool (4), resulting in smaller pieces of cut tissue which are easier to remove through the lumen (21).

18 Claims, 7 Drawing Sheets

SURGICAL SYSTEM AND METHOD

This invention relates to a surgical system, and to a method for removing tissue from a target site on or within a patient's body. In a preferred construction, the invention relates to an electrosurgical system and method that can use electrical and mechanical energy to treat tissue.

Known mechanical surgical instruments include simple scalpels which are used for cutting soft tissue, rotatable shavers which are also used for removing soft tissue, and rotatable burrs which are used for cutting harder tissue such as bone.

Known electrosurgical instruments include monopolar and bipolar devices, both of which are used primarily for treating or cauterising soft tissue. Typically, tissue is removed using a mechanical cutting device such as a shaver (or by an electrosurgical device operating in cutting or vaporisation mode), and then a cauterising device is used to coagulate tissue in order to stench bleeding.

It is known to use a surgical instrument which includes a mechanical element, such as a rotary shaver or burr, and an electrosurgical instrument such as a monopolar or bipolar device. A known instrument of this type is described in U.S. Pat. No. 5,904,681, which describes an instrument having a shaver or burr rotatably mounted within an outer sleeve, and a bipolar electrosurgical device mounted at the end of the outer sleeve and adjacent to an apertured end portion thereof through which the rotary shaver or burr acts on soft or hard tissue, or bone. The electrosurgical device can be used to cut or cauterise tissue as an alternative to the use of the shaver or burr.

Other devices which use a combination of electrosurgical and mechanical energy are described in U.S. Pat. No. 5,527,331, U.S. Pat. No. 6,159,209, U.S. Pat. No. 6,214,001 and WO97/33523. U.S. Pat. No. 5,527,331 describes a prostate treatment instrument which uses a rotary cutting blade which is also electrically active so that the device can resect tissue either by conventional cutting or by electrocautery. U.S. Pat. No. 6,159,209 describes a similar cutting blade which is used to cut, coagulate and vaporize prostate and bladder tissue, whilst allowing most of the excised tissue to be retrieved for histological examination. U.S. Pat. No. 6,214,001 describes another example of a rotating cutting blade which is electrically active. WO97/33523 describes an electrosutgical rotating cutting device in which the rotating blade is supplied with radio frequency energy to create a high-energy are discharge to assist with the incision of tissue.

The disadvantage of each of these prior art instruments is that tissue debris created by the device cannot easily be removed from the vicinity of the surgical site via the sleeve interior by the source of suction provided.

The aim of the present invention is to provide a method and apparatus in which tissue debris may be more easily and effectively be removed from a surgical site with less tendency for the device to become blocked by tissue.

Accordingly a method of removing tissue from a target site on or within a patient's body is provided, the method comprising the steps of:

a) applying heat to at least a portion of the target site so as to coagulate tissue therein, b) subsequently cutting coagulated tissue from the target site into relatively small pieces, and c) removing the relatively small pieces from the target site.

It has been found that, by coagulating the tissue to be removed before cutting it, the pieces produced by the cutting action are generally smaller in size and easier to remove from the target site. Where the removal is carried out via a suction tube, there is less tendency for the tube to become blocked by the pieces of cut tissue.

The coagulation of the tissue must be carried out prior to the step of cutting the tissue. This is directly contrary to the conventional wisdom in electrosurgery, in which the tissue is firstly cut, and then subsequently coagulated in order to stem bleeding. The coagulation may be performed as a preliminary procedure, or may be performed immediately prior to the cutting of tissue, preferably with the same surgical instrument.

The cutting of the tissue is conveniently performed by moving a mechanical cutting element, typically a rotatable cutter. Other methods of cutting which could feasibly be employed include laser cutting, ultrasonic cutting or radio frequency vaporisation.

The coagulation of the tissue may conveniently be performed by supplying a heated fluid to the target site, thereby causing coagulation of tissue at the target site.

Accordingly a method of removing tissue from a target site on or within a patient's body is provided, the method comprising the steps of:

a) supplying a fluid to the target site, b) heating the fluid so as to coagulate tissue at the target site, c) moving a mechanical cutting element so as to cut coagulated tissue from the target site into relatively small pieces, and d) removing the relatively small pieces from the target site.

Conveniently the fluid is an electrically-conductive fluid, and is heated by a radio frequency signal applied thereto.

The invention further resides in an electrosurgical system comprising:

a) a surgical instrument including a fluid supply means for supplying a fluid to a target site, a heating device capable of heating the conductive fluid so as to coagulate tissue at the target site, a mechanical cutting device capable of cutting coagulated tissue at the target site into relatively small pieces, and suction means for removing tissue cut by the cutting device from the target site;

b) power generating means for providing power to the heating device;

c) drive means for the cutting device; and d) a controller for the power generating means and the drive means, the controller controlling the power generating means and the drive means such that tissue at the target site is coagulated by the fluid heated by the heating device prior to being cut by the cutting device.

The invention further resides in an electrosurgical system comprising:

a) a surgical instrument including a fluid supply means for supplying a conductive fluid to a target site, an electrosurgical device capable of heating the conductive fluid so as to coagulate tissue at the target site, a mechanical cutting device capable of cutting coagulated tissue at the target site into relatively small pieces, and suction means for removing tissue cut by the cutting device from the target site;

b) power generating means for providing a high frequency voltage to the electrosurgical device;

c) drive means for the cutting device; and d) a controller for the power generating means and the drive means, the controller actuating the power generating means simultaneously with the drive means such that tissue at the target site is coagulated by the fluid heated by the electrosurgical device prior to being cut by the cutting device.

Conveniently, the electrosurgical device is a bipolar electrosurgical device including at least one active electrode, at least one return electrode and an insulator for spacing and insulating the or each return electrode with respect to the or each active electrode. The electrosurgical instrument heats the conductive fluid, typically saline, supplied to the target site, and the heated fluid causes tissue at the target site to coagulate prior to being cut.

The cutting device is preferably a rotatable cutting element, conveniently mounted on a hollow elongate cylindrical member. The hollow member typically acts as a lumen for the suction means to allow small pieces of tissue cut by the cutting element to be evacuated from the target site. As stated earlier, the prior coagulation of the tissue ensures that the cut tissue is relatively small in diameter. In particular, the prior coagulation of the tissue means that the maximum size of the resulting pieces of tissue is reduced, and the number of relatively large particles produced is much less than the number produced by the cutting of uncoagulated tissue.

The hollow member is preferably housed for rotation within a second hollow cylindrical member, with corresponding apertures at the distal ends thereof in order to allow the rotating cutting element to contact the coagulated tissue. Preferably, at least one electrical contact is provided in the form of a commutator brush contact for supplying electrosurgical signals to the hollow cylindrical member as it is being rotated. Alternatively, at least one electrical contact is provided in the form of a fluid contact, adapted to supply electrosurgical signals directly to the electrically conductive fluid.

In a preferred arrangement, a third elongate cylindrical member is provided, the second and third members defining a lumen therebetween for the fluid supply means. Conductive fluid is supplied to the target site between the second and third cylindrical members, and heated in order to coagulate tissue at the target site. Where the fluid is heated by a bipolar electrosurgical device, the third cylindrical member conveniently comprises an active electrode, and the first or second cylindrical members conveniently comprise the return electrode. Typically, the second cylindrical member is provided with an electrically-insulating coating in order to act as the insulator between the active and return electrodes.

When a radio frequency signal is applied to the third cylindrical member, current flows through the conductive fluid to the first or second cylindrical members at the distal end thereof, causing the conductive fluid to be significantly heated. The heated fluid is in contact with the tissue at the target site, and causes coagulation of at least the surface layers of the tissue. When the cutting element is rotated, coagulated tissue is cut into relatively small pieces which are then evacuated from the target site by the suction means.

The invention will now be described in greater detail, by way of example, with reference to the drawings, in which.

Figure 1:
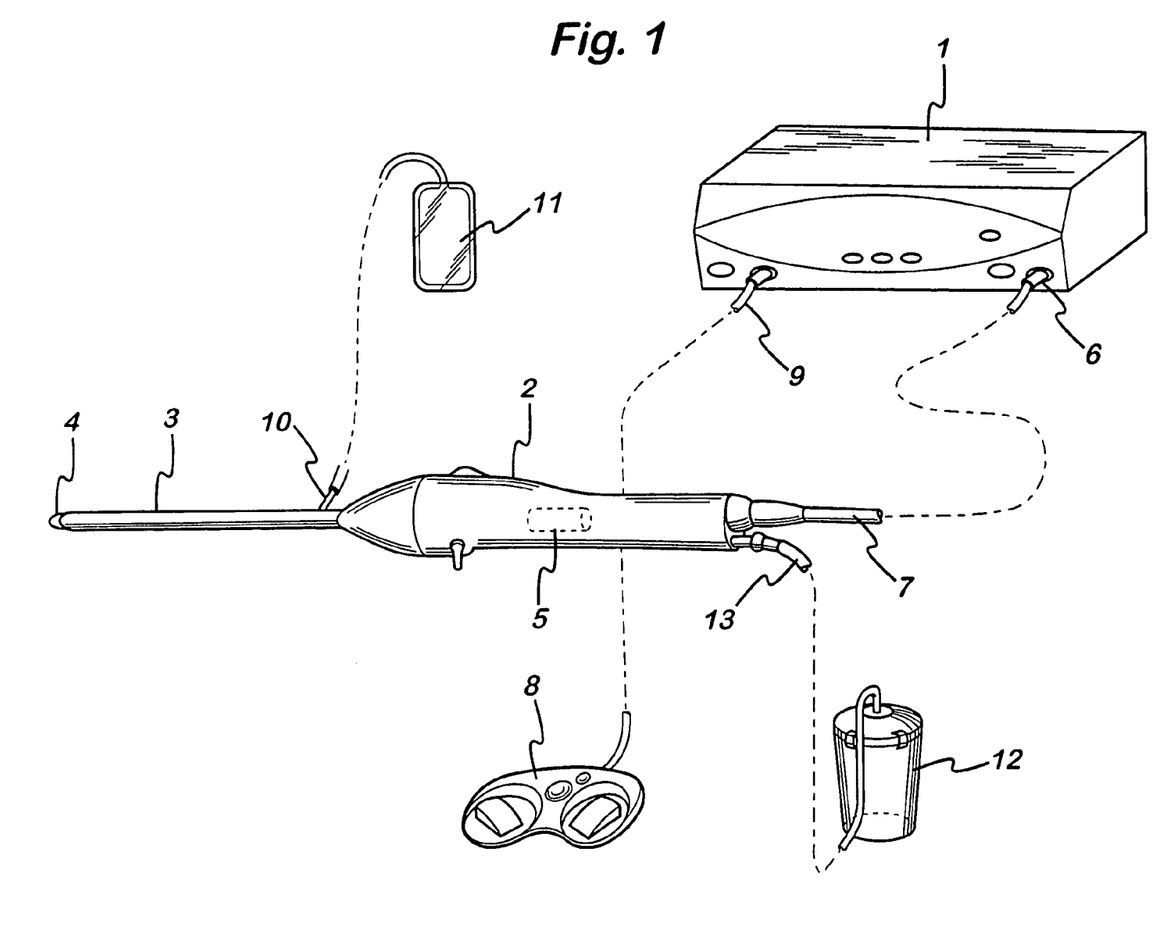
FIG. 1 is a schematic diagram of a surgical system incorporating a surgical instrument constructed in accordance with the invention.

Referring to the drawings, FIG. 1 shows an electrosurgical system which includes a controller/generator 1, and a handpiece 2 having a detachable surgical probe shown generally at 3. The probe 3 includes both a rotatable cutting element 4, driven by a motor shown schematically at 5 within the handpiece 2, and a bipolar electrosurgical device to be described in more detail later, Power signals for both the motor 5 and the electrosurgical device are supplied to the handpiece 2 from an output socket 6 on the generator 1, via a connector cord 7. Activation of the controller/generator 1 may be performed by means of a footswitch 8, coupled to the controller/generator 1 by means of a connector cord 9. An inlet port 10 allows saline to be fed from a saline source 11 to the distal end of the probe 3. A source of suction 12 is also provided, coupled to the handpiece by a cord 13.

Figure 2:
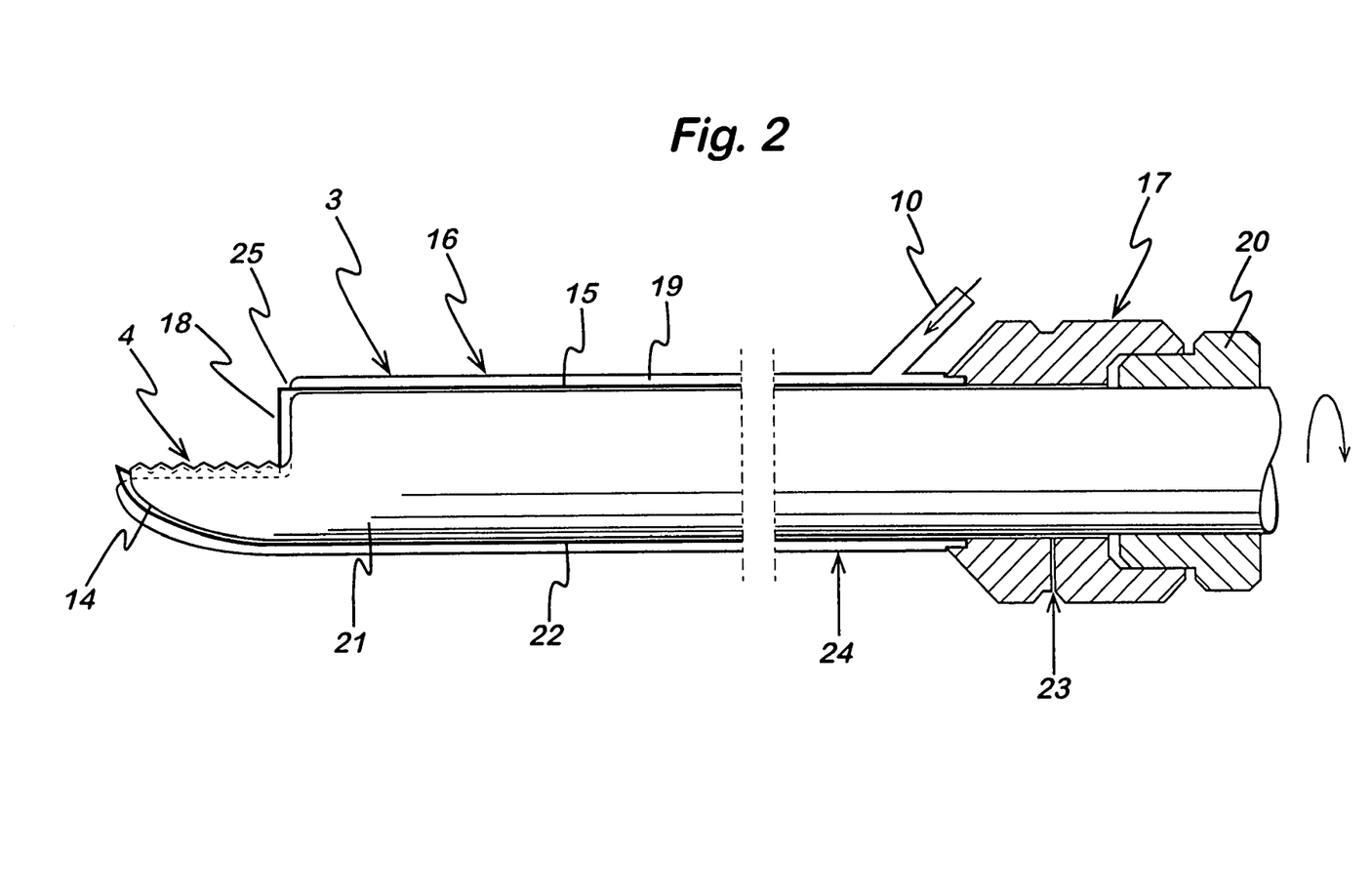
FIG. 2 is a side view, partly in section, of the distal end of a surgical instrument constructed in accordance with the invention.

FIG. 2 shows the distal end of the surgical probe 3 which is basically constituted by three hollow cylindrical tubes 14, 15 and 16. The outer tubes 15 and 16 are mounted at their proximal ends on a stationary hub 17 which constitutes the distal portion of the handpiece 2. Each of the tubes 15 and 16 has an aperture 18 at the distal end thereof. The tubes 15 and 16 are coaxial and define a channel 19 therebetween. The channel 19 communicates with the aperture 18 at its distal end, and the inlet port 10 at its proximal end, thereby providing a saline feed channel from the saline source 11 via the port 10 to the distal end of the probe 3.

The inner tube 14 is mounted for rotation within the middle tube 15, via a rotatable hub 20 which is driven by the motor 5. The inner tube 14 carries the cutting element 4 at its distal end, the cutting element being accessed through the apertures 18 in the tubes 15 and 16. The inner tube 14 also defines a central lumen 21 which is connected through the hub 20 to the suction source 12. The three tubes 14, 15 and 16 are made of an electrically-conducting material such as metal, but the middle tube 15 is provided with a coating 22 of electrically-insulating material such as PFTE on its outer surface. This coating 22 serves to insulate electrically the inner tube 14 from the outer tube 16. The tubes 15 and 16 are provided with respective connections 23 and 24, so that radio frequency signals from the controller/generator 1 can be supplied thereto. In this way, the outer tube 16 acts as the active electrode of the electrosurgical device, and the middle tube 15 and the inner tube 14 jointly act as the return electrode, the tubes 15 and 16 being in intimate electrical contact one with the other. In this way, the connection 23 can be made to the stationary tube 15, and the need for a commutator connection to rotatable tube 14 is avoided. The insulating coating 22 on the outside of the middle tube 15 serves to prevent shorting between the active outer tube 16 and the tubes 14 and 15.

The surgical instrument described above is intended for ENT surgery, that is to say for operations within the mouth or throat. It will be appreciated, however, that the surgical instrument could be used at any surgical site located within the body of a patient where surgery is to be performed, including arthroscopic use, i.e. on joints such as shoulders or knees. Moreover, the surgical instrument is primarily intended for use with an endoscope which allows a surgeon to view a surgical site. In such a case, the surgical instrument is inserted through a first incision, and the endoscope is inserted through a second incision. The distal ends of both the endoscope and the surgical instrument are positioned adjacent to the surgical site, and the surgeon can view the surgical site on a monitor attached to the endoscope.

In use, once the endoscope and surgical instrument have been positioned adjacent to the surgical site, saline is fed from the source 11 via the inlet port 10, the channel 19, and the apertures 18 to the surgical site. The surgeon depresses the footswitch 8 to send a signal to the controller/generator 1 so that a radio frequency current is supplied to the handpiece 2. The RADIO FREQUENCY signal is provided via the connections 22 and 23 to the middle and outer tubes 15 and 16 respectively. Current flows from the outer tube 16 through the saline to the middle tube 15, heating the saline in region 25 and hence heating tissue at the surgical site, thereby causing it to become coagulated.

Simultaneously with the supply of the RADIO FREQUENCY signal, or alternatively following a short predetermined delay, the controller/generator 1 activates the motor 5 in order to rotate the inner tube 14 and hence the cutting element 4. The rotation of the cutting element 4 causes coagulated tissue at the surgical site to be cut into small pieces. The small pieces of tissue, together with saline fed from the channel 19, are removed from the surgical site through the lumen 21 by the source of suction 12. It is a recognized problem with this type of instrument that pieces of cut tissue can cause the lumen 21 to become blocked. This problem is minimised by the present instrument, which pre-coagulates the tissue, causing the size of the cut tissue particles to be smaller than when cutting uncoagulated tissue. The smaller sized pieces of tissue are therefore more easily accommodated by the lumen 21, and conducted away from the surgical site with less chance of the lumen becoming blocked.

Figure 3A:
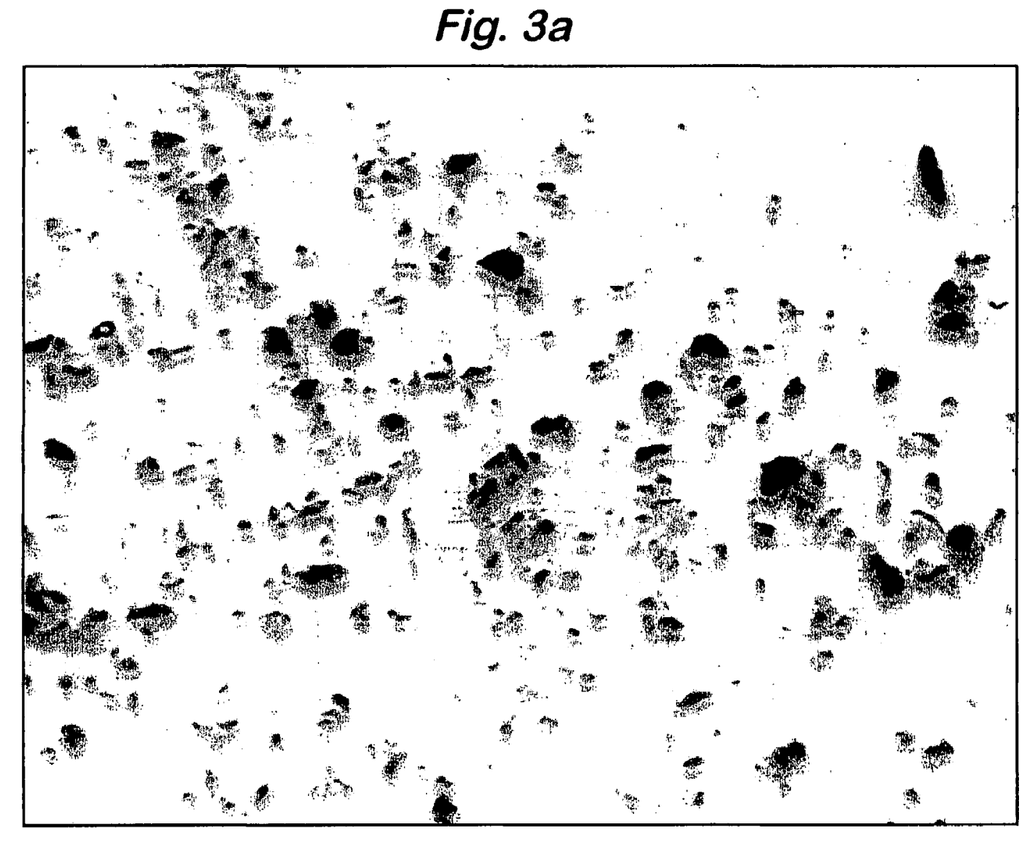
FIG. 3a is a photograph of tissue particles produced from the instrument of FIG. 2, the particles being cut without pre-coagulation.

FIG. 3a shows the tissue pieces extracted from the instrument of FIG. 2 when pre-coagulation was not employed. The cutting blade, which was a 4 mm outside diameter Smith & Nephew irrigating blade incisor (Serial No. 7032-6850), was rotated at 1400 r.p.m. using a Turbo 7000 controller. Saline was fed to the tip of the shaver at a flow rate of 18 ml/minute, and suction was applied to the central lumen to a level of 4.5 inches Hg. The shaver was used to remove approximately 1 g of tissue from a fresh pig's liver, and the tissue is shown in FIG. 3a against a grid having a 5 mm grid side dimension. As can be seen from the photograph, tissue particles of varying sizes were produced, some having a dimension of up to 8 mm. A significant proportion of the particles have at least one dimension over 5 mm.

Figure 3B:
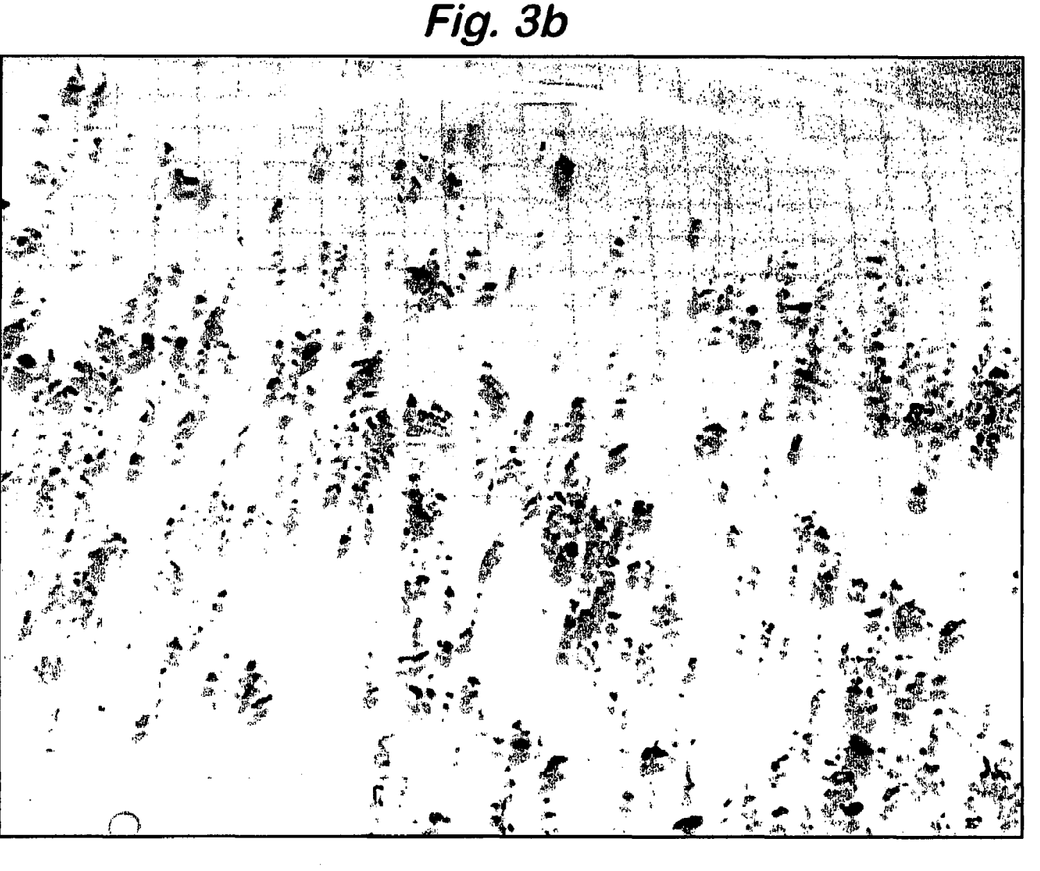
FIG. 3b is a photograph of tissue particles produced from the instrument of FIG. 2, the particles being cut following pre-coagulation.

In contrast, the same instrument was used on the same pig's liver and under the same conditions except for the addition of radio frequency energy to the electrodes of the instrument. The signal was a nominal 350 kHz radio frequency signal from a Gyrus Medical PK1 urology generator, operated at a 35 watt setting in coagulation mode. The instrument was used to remove tissue, with the radio frequency signal and rotational drive applied substantially simultaneously. The resulting tissue particles are shown in FIG. 3b, again on a 5 mm grid. As can be clearly seen from the Figures, the particle size of the pre-coagulated tissue is significantly smaller, with most of the particles being under 3 mm. The largest particles are less than 4 mm, with very few being over 3 mm. Thus, the particles of FIG. 3b will be more easily extracted from the surgical site, with less likelihood of them blocking the suction lumen of the instrument.

Figure 4:
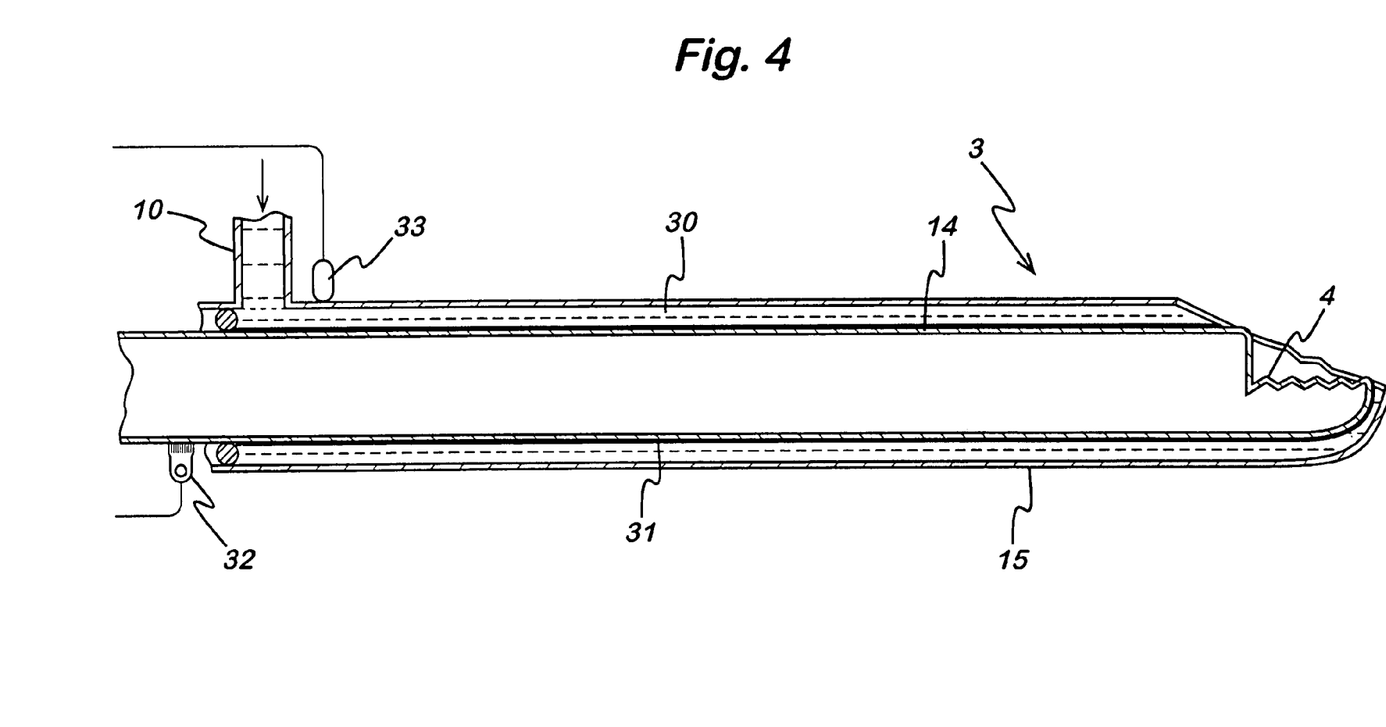
FIGS. 4 to 6 are schematic sectional side views of alternative embodiments of surgical instrument in accordance with the present invention.

The instrument of FIG. 4 is similar in some ways to that of FIG. 2, and like parts are designated with like reference numerals. The device has the hollow cylindrical tubes 14 and 15; but, instead of a third tube 16, the instrument of FIG. 4 uses the channel 30 between the tubes 14 and 15 to carry saline to the distal end of the probe 3. The inner tube 14 is coated on its external surface with an insulating coating 31, and a commutator brush contact 32 is in electrical contact with an uncoated portion of the tube 14 as it is rotated by the motor. In this way, radio frequency signals are supplied to the inner tube 14 as it rotates, such that it becomes the active electrode of the electrosurgical device. The outer tube 15 serves as the return electrode, and is connected to the electrosurgical generator 1 by means of a stationary contact 33. The insulating coating 31 acts to insulate the cylindrical tubes 14 and 15 one from the other even when an electrically-conductive fluid such as saline is present therebetween in the channel 30.

As before, the radio frequency signal supplied to the saline at the distal end of the instrument heats the saline, and causes a coagulation of the tissue adjacent to the instrument. This in turn results relatively small pieces of tissue being produced by the cutting action of the mechanical cutting element 4.

Figure 5:
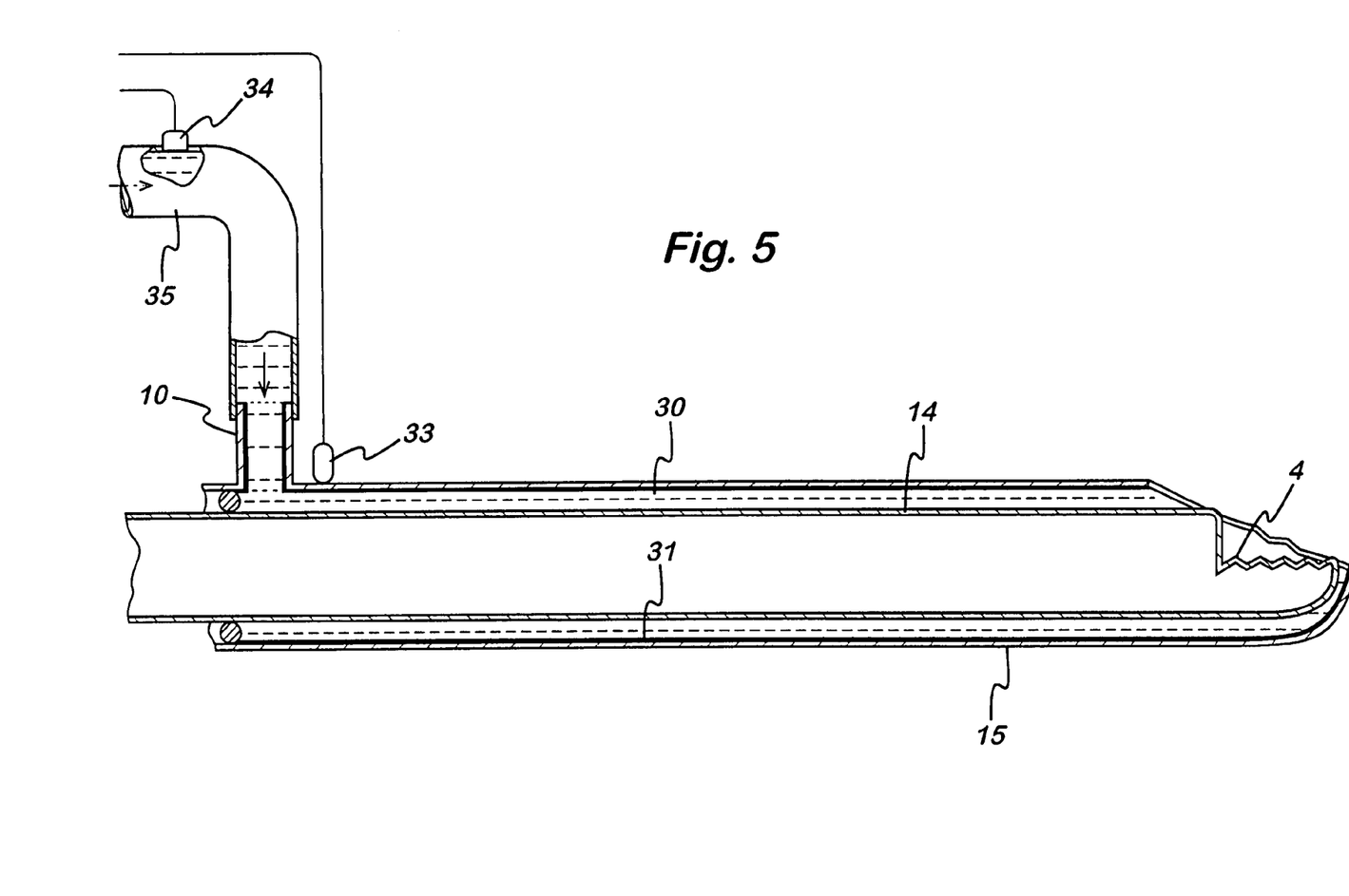

FIG. 5 shows an alternative arrangement, in which the brush contact 32 is dispensed with, and the radio frequency signal is applied via the conductive fluid itself. An electrical contact 34, inserted into a saline feed tube 35 delivers the radio frequency signal to the saline, which enters the channel 30 between the tubes 14 and 15 as in FIG. 4. The insulating coating 31 is in this embodiment present on the inner surface of the outer tube 15, such that the saline is in electrical communication with the inner tube 14 but not the outer tube 15. As before, an electrical contact 33 on the outer surface of the tube 15 completes the electrical circuit, such that the saline is heated by the radio frequency signal as it emerges from the channel 30 at the distal end of the instrument. The tissue effect is as previously described, with smaller particles of tissue being produced by the cutting element 4.

Figure 6:
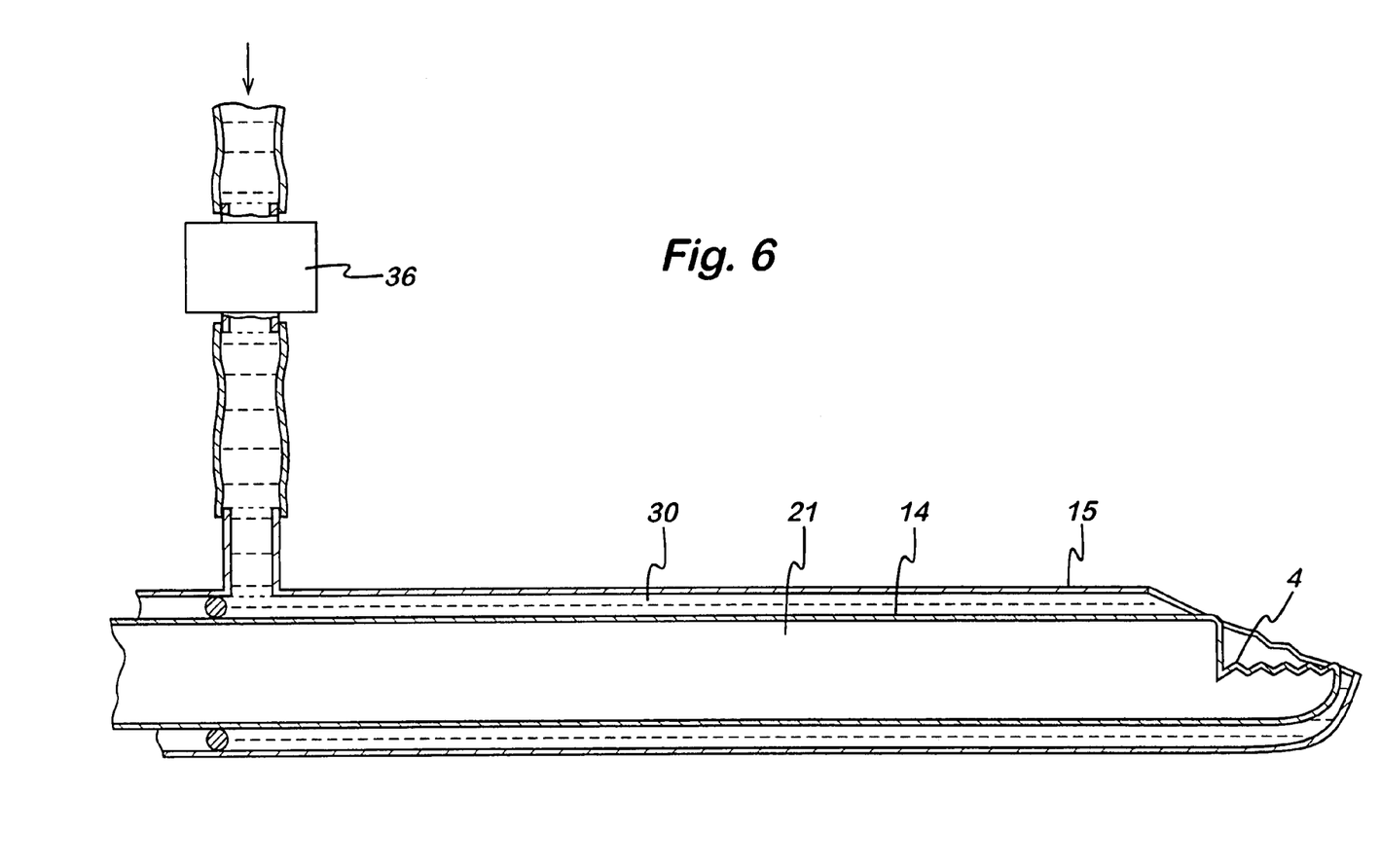

FIG. 6 shows another embodiment in which a heating means 36, which may be a resistive or inductive heating element rather than a radio frequency signal, is used to heat the fluid emerging from the channel 30. In this embodiment, the requirement for electrical contacts on the tubes 14 and 15 is obviated, as there is no radio frequency signal applied thereto. This also means that the fluid in the channel 30 does not necessarily need to be a conductive fluid such as saline, and indeed can conceivably be sterile deionised water. The fluid emerging from the channel 30 at the distal end of the instrument can therefore be a hot liquid, or even a gas such as steam. In whichever event, the heated fluid coagulates the tissue simultaneously or prior to mechanical cutting by the cutting element 4, thereby producing smaller tissue particles to be evacuated from the surgical site through the central lumen 21.

The invention has been described with reference to a rotary shaver, but it will be appreciated by those skilled in the art that the invention can equally be employed with other surgical cutting devices, such as burrs, drills etc. Indeed, the cutting device need not necessarily be mechanical, and other cutting techniques such as laser, ultrasound or purely radio frequency cutting may be employed as desired. The appreciation that the pre-coagulation of the tissue leads to smaller particle sizes can be an advantage whatever cutting technique is employed.

The invention claimed is:

1. A method of removing tissue from a target site on or within a patient's body comprising the steps of:
   a) supplying a fluid to the target site,
   b) heating the fluid so as to coagulate tissue at the target site,
   c) moving a rotating mechanical cutting element so as to cut coagulated tissue from the target site into relatively small pieces, and
   d) removing the relatively small pieces from the target site.

2. A method according to claim 1 wherein the fluid is an electrically conductive fluid and is heated by a radio frequency signal applied thereto.

3. An electrosurgical system comprising:
   a) a surgical instrument including a fluid supply means for supplying a fluid to a target site, a heating device capable of heating the fluid so as to coagulate tissue at the target site, a mechanical cutting device capable of cutting coagulated tissue at the target site into relatively small pieces, and suction means for removing tissue cut by the cutting device from the target site;
   b) power generating means for providing power to the heating device;
   c) drive means for the cutting device; and
   d) a controller for the power generating means and the drive means, the controller controlling the power generating means and the drive means such that tissue at the target site is coagulated by the fluid heated by the heating device prior to being cut by the cutting device.

4. An electrosurgical system comprising:
   a) a surgical instrument including a fluid supply means for supplying a conductive fluid to a target site, an electrosurgical device capable of heating the conductive fluid so as to coagulate tissue at the target site, a mechanical cutting device capable of cutting coagulated tissue at the target site into relatively small pieces, and suction means for removing tissue cut by the cutting device from the target site;
   b) power generating means for providing a high frequency voltage to the electrosurgical device;
   c) drive means for the cutting device; and
   d) a controller for the power generating means and the drive means, the controller actuating the power generating means simultaneously with the drive means such that tissue at the target site is coagulated by the fluid heated by the electrosurgical device prior to being cut by the cutting device.

5. An electrosurgical system according to claim 4 wherein the cutting device is a rotatable cutting element.

6. An electro surgical system according to claim 5 wherein the cutting element is mounted on a hollow elongate cylindrical member.

7. An electrosurgical system according to claim 6 wherein the hollow cylindrical member acts as a lumen for the suction means.

8. An electro surgical system according to claim 6 wherein the hollow cylindrical member is housed for rotation within a second hollow cylindrical member.

9. An electro surgical system according to claim 8 wherein the hollow cylindrical member and the second hollow cylindrical member define a lumen therebetween for the fluid supply means.

10. An electrosurgical system according to claim 9 wherein the electrosurgical device is a bipolar electrosurgical device including at least one active electrode, at least one return electrode and an insulator for spacing and insulating the or each return electrode with respect to the or each active electrode.

11. An electrosurgical system according to claim 10 wherein the hollow cylindrical member constitutes the at least one active electrode, and the second hollow cylindrical member constitutes the at least one return electrode.

12. An electro surgical system according to claim 11 wherein at least one cylindrical member is provided with an electrically insulating coating in order to act as the insulator between the active and return electrodes.

13. An electrosurgical system according to claim 12 wherein there is provided at least one electrical contact in the form of a commutator brush contact, for supplying electrosurgical signals to the hollow cylindrical member as it is being rotated.

14. An electrosurgical system according to claim 12 wherein there is provided at least one electrical contact in the form of a fluid contact, adapted to supply electrosurgical signals directly to the electrically conductive fluid.

15. An electrosurgical system according to claim 8 wherein there is provided a third elongate cylindrical member, the second and third cylindrical members defining a lumen therebetween for the fluid supply means.

16. An electrosurgical system according to claim 15 wherein the electrosurgical device is a bipolar electrosurgical device including at least one active electrode, at least one return electrode and an insulator for spacing and insulating the or each return electrode with respect to the or each active electrode.

17. An electrosurgical system according to claim 16, wherein the third cylindrical member comprises the at least one active electrode, and the first or second cylindrical member comprises the at least one return electrode of the electrosurgical device.

18. An electrosurgical system according to claim 17 wherein the second cylindrical member is provided with an electrically insulating coating in order to act as the insulator between the active and return electrodes.

* * * * *